United States Patent [19]

Arena et al.

[11] 4,416,992

[45] Nov. 22, 1983

[54] SUPPORT MATRICES AND IMMOBILIZED ENZYME SYSTEMS

[75] Inventors: Blaise J. Arena, Des Plaines; Ronald P. Rohrbach, Forest Lake, both of Ill.

[73] Assignee: UOP Inc., Des Plaines, Ill.

[21] Appl. No.: 362,206

[22] Filed: Mar. 26, 1982

[51] Int. Cl.³ ............... C12N 11/14; C12N 11/08; C12N 11/06
[52] U.S. Cl. ............... 435/176; 435/180; 435/181
[58] Field of Search ............... 435/174, 176, 177, 179, 435/180, 181

[56] References Cited

U.S. PATENT DOCUMENTS 3,841,969  10/1974  Emery et al. ............... 435/179 X
4,268,419   5/1981  Rohrbach ............... 435/176 X
4,337,172   6/1982  Teague et al. ............... 435/176 X

OTHER PUBLICATIONS

J. M. S. Cabral et al., *Biotechnology and Bioengineering*, 23, 2083 (1981).

*Primary Examiner*—David M. Naff
*Attorney, Agent, or Firm*—James R. Hoatson, Jr.; Eugene I. Snyder; William H. Page, II

[57] ABSTRACT

Support matrices are prepared by titanating the surface hydroxyl groups of refractory inorganic oxides with a titanium tetrahalide, such as $TiCl_4$, reacting each of the remaining halogens of the surface-titanated oxide with one of the amino groups of diamine, and thereafter reacting the remaining amino group with one of the functional groups of a dialdehyde or diisocyanate. Titanating is carried out by contacting a refractory inorganic oxide with titanium tetrahalide, preferably in the absence of a solvent for the titanium tetrahalide, removing excess and unreacted titanium tetrahalide and heating the titanated inorganic oxide at a temperature of from about 80° C. to about 200° C. in an inert atmosphere of nitrogen, argon or helium, or in a vacuum. Such support matrices may be used to bind enzymes, affording effective immobilized enzyme systems.

34 Claims, No Drawings

SUPPORT MATRICES AND IMMOBILIZED ENZYME SYSTEMS

BACKGROUND OF THE INVENTION

Because enzymes can catalyze chemical transformations so effectively, there is increasing emphasis on the use of enzyme reactions in commercial processes. The relatively high cost of enzymes demands their reuse. Typically, if the reaction is performed under homogeneous conditions recovery of enzyme is difficult and expensive, which effectively precludes homogeneous enzymatic catalysis. The solution to this problem is to insolubilizer enzyme under conditions where a substantial portion of the enzymatic activity exhibited in solution remains under heterogenous reaction conditions.

One particular solution to the aforementioned problem is the construction of immobilized enzyme systems. An immobilized enzyme system consists of a support matrix to which there is bound an enzyme. A support matrix is a structure characterized as having good physical integrity and favorable properties toward liquid flow under conditions experienced in fixed bed reactors, and further characterized by having the ability to bind or immobilize enzymes with minimum perturbation of enzymatic action. By an immobilized enzyme system is meant the structure which results from immobilization of an enzyme on a support matrix.

The binding or immobilization of enzymes to a support matrix is represented by the extremes of physical and chemical binding forces. It is to be recognized that in most cases enzyme immobilization arises from a combination of such binding forces, although often one such force predominates, with the nature of enzyme immobilization generally being determined by the nature of the support matrix. As an example, when the support matrix is a resin, such as one of the phenol-formaldehyde type, binding is predominantly through physical forces. A similar result is obtained when the support matrix is of an ion exchange type. Where the support matrix is comprised of refractory inorganic material, such as inorganic oxides, glass, and ceramics, bearing or impregnated with organic material, for example, polyamines, either bearing pendant functional groups themselves or cross-linked with a bifunctional reagent which provides pendant functional groups, enzyme immobilization arises mainly by chemical reaction of a site on the enzyme with the pendant functional group so as to form a covalent bond. In such an instance binding is, at least predominantly, by chemical means.

Recently Cabral and co-workers, *Biotechnology and Bioengineering*, 23, 2083 (1981) described metal-link-activated inorganic supports as support matrices, especially controlled-pore glass treated with titanium tetrachloride, subsequently dried in air, then reacted with hexamethylenediamine followed by glutaraldehyde. Although the support matrices described herein are superficially similar, they are operationally different and distinct from the prior art matrices, as shown by direct comparison with the support matrix prepared according to Cabral et. al.

The object of this invention is to prepare support matrices for immobilized enzymes and other reactive entities, and to prepare immobilized enzyme systems thereform. An embodiment is a method comprising contacting a porous inorganic refractory oxide with a titanium tetrahalide, removing excess and unreacted titanium tetrahalide by means including heat in an inert atmosphere at between about 80° and 200° C., contacting the resulting titanated alumina with a diamine or other polyamine, removing unreacted amine, contacting the mass with a bifunctional monomer, and recovering the resulting support matrix.

The purpose of the method described is to react surface hydroxyl groups from a porous refractory inorganic oxide with a titanium tetrahalide, $TiX_4$, to afford a surface coating of $Al-O-TiX_y$ species. This surface coating has little effect on the surface properties of the inorganic oxide, yet provides a chemically reactive halide to other reagents. Diamines are an example of other reagents which react with the titanium-bonded halide, with one amino group firmly bound to the inorganic oxide via a strong titanium-nitrogen bond, and the other amino group subsequently reacting with a bifunctional reagent whose other functional moiety is available for covalent bonding to an enzyme.

Among the desirable properties of the resulting immobilized enzyme system is that the enzyme is held well away from the surface, thereby maximizing its opportunity to behave as it does in homogeneous reactions, and that the enzyme is covalently bonded to the support matrix, which generally imparts relatively high stability. An important difference between the support matrices and immobilized enzyme systems described here and those of the prior art is that drying of the titanated oxide is performed in an inert atmosphere, thereby preserving all titanium-halogen bonds. The prior art method assures that few, if any, titanium-halogen bonds will be present on the support matrix precursor.

DESCRIPTION OF THE INVENTION

Our invention is a method of preparing a support matrix comprising contacting a refractory inorganic oxide with a titanium tetrahalide so as to produce a surface-titanated oxide, removing excess, unreacted titanium tetrahalide, heating the titanated inorganic oxide at a temperature from about 80° to about 200° C. in an inert atmosphere for a time sufficient to volatilize the remaining unreacted titanium tetrahalide, contacting the resulting material with a diamine or polyamine whose formula is $H_2N(CH_2CH_2NH)_xH$, removing excess amine, treating the resulting mass with an excess of a bifunctional reagent, removing the excess and unreacted bifunctional reagent, and recovering the resulting support matrix. In another aspect our invention is the support matrix prepared by the described method. In still another aspect this invention deals with the preparation of an immobilized enzyme system from the support matrices described herein. In yet another aspect our invention is the immobilized enzyme system as prepared by the method of our invention.

The support matrices of this invention are prepared by a method whose first step is that of contacting a porous refractory inorganic oxide selected from the group consisting of alumina, silica, titania, thoria, and combinations thereof, with a titanium tetrahalide. Alumina generally has been found to be the most convenient inorganic oxide for use in this invention. Titanium tetrafluoride, tetrachloride, and tetrabromide may be used in the practice of this invention, although titanium tetrachloride is the most desirable material. The purpose of contacting with titanium tetrahalide is to produce a surface-titanated oxide. Contacting may be performed with neat titanium tetrahalide where the material is liquid under the conditions of contacting. Solutions of titanium tetrahalide may be used but not necessarily with equivalent results. Among the solvents which may be used with, for example, titanium tetrachloride, are cold water, alcohols, amines, and ethers. Where water and alcohol is used there is a competitive reaction between the surface hydroxyl groups of the inorganic oxide and the solvent hydroxyl groups. A similar competitive reaction occurs where the amine is primary or secondary. Tertiary amines and ethers are not reactive with titanium tetrahalides in the sense of failing to form strong covalent bonds with titanium, but both coordinate strongly with titanium tetrahalides forming Lewis acid-base complexes which can alter the results relative to the use of neat titanium tetrahalide. Therefore, it is preferred that no solvent be used in this contacting step. A contact time up to about 1 hour at room temperature is generally sufficient.

Excess and unreacted titanium tetrahalide is then removed, typically by decantation of excess liquid. However, a solvent wash is possible where the solvent is unreactive under the conditions of washing. Where ethers or tertiary amines are used, coordination compounds may form which subsequently adhere to the inorganic oxide and influence the later steps in the preparation of the support matrix. It is not to be expected that a solvent wash where a complex forms will necessarily give results equivalent to simple decantation.

The titanated inorganic oxide from which excess titanium tetrahalide has been removed by decantation or solvent wash is then heated in an inert atmosphere to volatilize the remaining adhering but unreacted titanium tetrahalide. It is essential to heat the material in an inert atmosphere to retain the titanium-halide bond(s), and especially to prevent hydrolysis of that bond. Among the gases which may be used to provide an inert atmosphere are nitrogen, argon, and helium. It is also possible to provide an inert atmosphere by heating the material in vacuum. Heating typically is done at a temperature from about 80° to about 200° C., with temperatures substantially in excess of 200° C. being undesirable because of chemical reactions which may occur at these elevated temperatures. Although the time necessary to volatilize adhering but unreacted titanium tetrahalide will depend on the temperature, a time less than about 2 hours generally suffices at a temperature of 150° C.

The resulting titanated inorganic oxide bearing reactive titanium-halogen bonds is then contacted with a diamine or other polyamine. Support matrices of this invention prepared from a diamine differ from those prepared using other types of polyamines, e.g., ethyleneimines of the formula $H_2N(CH_2CH_2NH)_xH$, $x>2$, in that the latter matrices bear an excess of positive charges. This results from the unreacted secondary amino groups (and tertiary amino groups if present) having a $pK_a$ whose value ensures substantial protonation of that group at a pH less than about 9. Where such excess positive charge is detrimental to the enzyme subsequently attached thereto, e.g., glucoamylase, it is beneficial to use a support matrix prepared from a diamine. Conversely, where excess positive charge is advantageous it is beneficial to use a support matrix prepared from a polyamine. Consequently it is seen that the support matrices of this invention present the novel advantage of being either positively charged or neutral depending upon the type of amine used in its preparation.

Alkylene diamines containing up to about 10 carbon atoms are especially effective diamines, and within this class unbranched diamines are preferred. These preferred materials have the formula $H_2N(CH_2)_nNH_2$, where n an integer from 2 to about 10, with n from about 4 to about 8 being especially preferred and those with n=4, 5, or 6 being particularly desirable. Examples of such diamines include 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, and 1,10-diaminodecane. The phenylene diamines also may be used successfully in the practice of this invention.

Among the polyamines which may be used in this invention are ethyleneimines of the formula $H_2N(CH_2CH_2NH)_xH$, where x is an integer other than 1. Polyamines where x is from 2 to about 5 are particularly useful, and correspond to materials as diethylenetriamine, triethylenetetramine, tetraethylenepentamine, and pentaethylenehexamine. In another variation the polyamine may be a polyethyleneimine of molecular weight from about 600 to about 100,000. That is, the value of x in the above formula is from about 13 to about 2300.

The amount of diamine used is not critical, but generally at least 3 molecules of diamine per titanium-bonded halogen are utilized. The amines may be used neat, so long as they are non-viscous liquids, or may be used in solution. Where used in solution any solvent is acceptable so long as it is unreactive with both the amine and titanated inorganic oxide. As an example organic ethers are generally acceptable solvents. The efficacy of the support matrix so prepared may depend somewhat on the nature of the solvent, the concentration of amine, and the pH of the solution, and optimum conditions can be readily determined by routine experimentation.

The next step in the preparation of the support matrices of this invention is to remove excess diamine, that is, unreacted but adhering diamine. Generally such removal occurs by decantation or a solvent wash, or some combination of both. Washing with water is quite effective in removing excess diamine, although alcohols, ethers, and other unreactive organic solvents may be used.

The resulting mass is then contacted with a bifunctional monomeric reagent. Among such reagents the classes of dialdehydes and diisocyanates are preferred, especially those of the formula $OHC(CH_2)_pCHO$ and $O=C=N(CH_2)_pNCO$, where p is from 2 to about 8, and the phenylene analogs, phthalaldehyde and toluene isocyanate. Preferred dialdehydes include succindialdehyde, glutaraldehyde, and adipaldehyde, with glutaraldehyde often being the dialdehyde of choice.

Excessive bifunctional reagent is then removed, typically by washing with a suitable solvent, among which water is the prime example. After complete removal of unreacted but adhering bifunctional reagent, the material is dried, generally in air at ambient temperature. At this point preparation of the support matrix is complete.

The immobilized enzyme systems of this invention comprise the support matrix previously described with an enzyme bound thereto. Examples of suitable enzymes which may be used in this invention, which are illustrative and not exclusive, include glucose isomerase, glucoamylase, cholesteroloxidase, alcohol dehydrogenase, amino acid oxidase, arginase, asparaginase, catalase, chymotrypsin, cellulase, collagenase, deoxyribonuclease, ficin, histidase, glucose oxidase, lactase, peroxidase, lysozyme, amylase, papain, rennin, ribonuclease, and urease.

To prepare an immobilized enzyme system, the support matrix may be contacted with an enzyme solution with mixing at a temperature from about 0° to about 70° C. for a period from about 5 to about 50 hours. The excess enzyme solution is removed, as by decantation, and the remaining solid may be washed with copious quantities of water or salt solution to remove adhering but unbound enzyme, with the solid thereafter recovered to afford the immobilized enzyme system.

The following examples are merely illustrative of this invention and do not limit it in any way.

EXAMPLES

Alumina of 60-80 mesh (30 cc) was covered with liquid $TiCl_4$ at room temperature under a nitrogen atmosphere. After 10 minutes excess liquid was removed by decantation. The resulting powder was placed in a furnace under nitrogen flow for 1 hour at 150° C. to afford a titanated alumina containing 8.64% titanium.

To 1 gram of the material prepared above was added 2.75 grams of neat 1,5-diaminopentane. After 16 hours at room temperature, excess diamine was removed by thorough washing with water. The resulting material was treated with 10 ml of 5% glutaraldehyde solution, pH 7.0, in a phosphate buffer. After one hour reaction the excess glutaraldehyde was removed by decantation and the solid was thoroughly washed with water to remove unreacted but adhering glutaraldehyde. Immobilized glucoamylase was prepared by adding a solution of the enzyme at 11.8 units per ml at pH 3.5 and at a total offering at 176 units per gram of support matrix. After 16 hours excess glucoamylase was removed by decantation, and the resulting immobilized enzyme system was washed well with water and a starch solution to remove excess unbound enzyme. The resulting immobilized enzyme system was packed into a reactor.

Immobilized glucoamylase systems were assayed in a plug flow differential reactor thermostated at 55° C. using as a feedstock Maltrin 150, a partially hydrolyzed starch of DE 15, buffered to pH 4.2. The assay consisted of measuring the initial rate of hydrolysis of starch to produce glucose. One unit of activity corresponds to 1 g glucose produced per hour.

The maximum glucose conversion was determined by the following batch recycle technique. Approximately 0.5 g immobilized enzyme in a thermostated differential plug flow reactor was washed with starch feedstock for 16 hr at 55° C. in a single pass to remove adsorbed enzyme. When washing was complete the feed was switched to a stirred reservoir containing 200 ml feedstock with effluent discharged into the reservoir. The flow rate was adjusted to a minimum linear velocity of 9.7 cm per minute to eliminate film diffusion resistance and to have a relatively small conversion per pass. The reservoir was sampled periodically for glucose to determine the maximum glucose attained. The immobilized glucoamylase as prepared above is designated as A in the Table below.

A titanated alumina support matrix was prepared in a manner similar to that above with the exception of there being an ether wash. To about 30 ml of alumina of 60-80 mesh under nitrogen was added enough $TiCl_4$ to cover the powder. After 10 minutes excess titanium tetrachloride was removed by decantation and the powder was washed repeatedly with ether, then vacuum dried. The dried powder was placed in a furnace under nitrogen and heated at 150° C. for 1 hour, after which the material showed 11.8% titanium.

One gram of this material was reacted with a 5% solution of 1,5-diaminopentane in tetrahydrofuran for 16 hours. Excess diamine was removed by thorough water washing, and the mass subsequently treated with glutaraldehyde as described for preparation A. Immobilized glucoamylase was prepared similar to the method above except that the enzyme was offered at 151 units per gram at pH 5.5. The resulting immobilized glucoamylase is designated as preparation B in the Table.

Preparation of a support matrix and an immobilized enzyme system according to the method of Cabral et al. proceeded as follows. To 5 grams of 60-80 mesh alumina was added 16.6 ml of a 15% w/v solution of $TiCl_4$ in concentrated hydrochloric acid. The slurry was mixed well and transferred to a 1 inch diameter horizontal furnace tube and spread around the wall so as to form a thin layer. This was heated in air at 45° to 50° C. for 64 hours after which a white, dry powder was scraped off the walls of the tube which analyzed for 7.71% titanium.

This material was treated with 1,5-diaminopentane as described for the preparation of sample A. After excess diamine had been removed by thorough water washing, the material was dried and ground because of significant agglomeration during reaction with the diamine. The dried mass was reacted with excess glutaraldehyde, washed, then used to bind glucoamylase in exactly the same way as described for sample A. The resulting immobilized glucoamylase is designated as C in the table.

A comparison of the immobilized glucoamylase systems prepared above is found in the following table.

| | Immobilized Glucoamylase | | |
| --- | --- | --- | --- |
| | A | B | C |
| Enzyme offered, units/g | 176 | 151 | 176 |
| Enzyme loaded, units/g | 130 | 100 | 82.5 |
| Initial activity at 55° C., units/g | 49.4 | 53.7 | 24.5 |
| Maximum glucose | 93.7 | 93.1 | 91.1 |

The table clearly shows important operational distinctions between the immobilized glucoamylase systems of this invention and that prepared according to Cabral. For example, the support matrices of this invention show superior loading capability toward glucoamylase than does the support matrix of the prior art. The immobilized enzyme systems prepared here have at least twice the activity shown by the prior art material. Lastly, the immobilized glucoamylase systems of this invention show a maximum glucose formation greater than that of the prior art material. Although the difference may appear small, it is of great commercial importance since conversions of at least 92% often are required for a process to be economically feasible.

What is claimed is:

1. A method of preparing a support matrix comprising contacting a porous, refractory inorganic oxide selected from the group consisting of alumina, silica, titania, thoria, and combinations thereof, with titanium tetrahalide in the absence of a solvent for the titanium tetrahalide so as to produce a surface titanated inorganic oxide, removing excess and unreacted titanium tetrahalide, heating the titanated inorganic oxide at a temperature from about 80° to about 200° C. in an inert atmosphere of nitrogen, argon, helium, or in a vacuum, for a time sufficient to volatilize any remaining unreacted titanium tetrahalide, contacting the resulting material with a diamine, selected from the group of alkylene diamines containing from 2 to about 10 carbon atoms and phenylene diamine, or a polyamine of formula $H_2N(CH_2CH_2NH)_xH$, where x is an integer from 2 to about 2300, removing excess amine, treating the resulting material with an excess of a bifunctional reagent selected from the group consisting of phthalaldehyde, toluene diisocyanate, and $X(CH_2)_pX$, where X is an aldehyde, CHO, or isocyanate, NCO, functional group and p is an integer from 2 to about 8, removing the excess and unreacted bifunctional reagent, and recovering the resulting support matrix.

2. The method of claim 1 where the oxide is alumina.

3. The method of claim 1 where the diamine is an alkylene diamine whose formula is $H_2N(CH_2)_nNH_2$, where n is an integer from 2 to about 10.

4. The method of claim 3 where the diamine is selected from the group consisting of 1,4-diaminobutane, 1,5-diaminopentane, and 1,6-diaminohexane.

5. The method of claim 1 where the diamine is a phenylenediamine.

6. The method of claim 1 where the bifunctional reagent is selected from the group consisting of succindialdehyde, glutaraldehyde, adipaldehyde, phthalaldehyde, and phenylisocyanate.

7. The method of claim 1 where the halide of titanium tetrahalide is selected from the group consisting of fluorine, chlorine, and bromine.

8. The method of claim 7 where the halide of titanium tetrahalide is chlorine.

9. The method of preparing an immobilized enzyme system comprising contacting a porous, refractory inorganic oxide selected from the group consisting of alumina, silica, titania, thoria, and combinations thereof, with titanium tetrahalide in the absence of a solvent for the titanium tetrahalide so as to produce a surface-titanated inorganic oxide, removing excess and unreacted titanium tetrahalide, heating the titanated inorganic oxide at a temperature from about 80° to about 200° C. in an inert atmosphere of nitrogen, argon, helium, or in a vacuum, for a time sufficient to volatilize any remaining unreacted titanium tetrahalide, contacting the resulting material with a diamine selected from the group of alkylene diamines containing from 2 to about 10 carbon atoms and phenylene diamine, or a polyamine of formula $H_2N(CH_2CH_2NH)_xH$, where x is an integer from 2 to about 2300, removing excess amine, treating the resulting material with an excess of a bifunctional reagent selected from the group consisting of phthalaldehyde, toluene diisocyanate, and $X(CH_2)_pX$, where X is an aldehyde, CHO, or isocyanate, NCO, functional group and p is an integer from z to about 8, removing the excess and unreacted bifunctional reagent, contacting the resulting mass with an enzyme solution, and recovering the formed immobilized enzyme system.

10. The method of claim 9 where the oxide is alumina.

11. The method of claim 9 where the diamine is an alkylene diamine whose formula is $H_2N(CH_2)_nNH_2$, where n is an integer from 2 to about 10.

12. The method of claim 11 where the diamine is selected from the group consisting of 1,4-diaminobutane, 1,5-diaminopentane, and 1,6-diaminohexane.

13. The method of claim 9 where the diamine is a phenylenediamine.

14. The method of claim 9 where the bifunctional reagent is selected from the group consisting of succindialdehyde, glutaraldehyde, adipaldehyde, phthalaldehyde, and phenylisocyanate.

15. The method of claim 9 where the halide of titanium tetrahalide is selected from the group consisting of fluorine, chlorine, and bromine.

16. The method of claim 15 where the halide of titanium tetrahalide is chlorine.

17. The method of claim 9 where the enzyme is selected from the group consisting of glucose isomerase, glucoamylase, cholesteroloxidase, alcohol dehydrogenase, amino acid oxidase, arginase, asparaginase, catalase, chymotrypsin, cellulase, collagenase, deoxyribonuclease, ficin, histidase, glucose oxidase, lactase, peroxidase, lysozyme, amylase, papain, rennin, ribonuclease, and urease.

18. The support matrix prepared by the method of claim 1.

19. The support matrix of claim 18 where the oxide is alumina.

20. The support matrix of claim 18 where the diamine is an alkylene diamine whose formula is $H_2N(CH_2)_nNH_2$, where n is an integer from 2 to about 10.

21. The support matrix of claim 20 where the diamine is selected from the group consisting of 1,4-diaminobutane, 1,5-diaminopentane, and 1,6-diaminohexane.

22. The support matrix of claim 18 where the diamine is a phenylenediamine.

23. The support matrix of claim 18 where the bifunctional reagent is selected from the group consisting of succindialdehyde, glutaraldehyde, adipaldehyde, phthalaldehyde, and phenylisocyanate.

24. The support matrix of claim 18 where the halide of titanium tetrahalide is selected from the group consisting of fluorine, chlorine, and bromine.

25. The support matrix of claim 24 where the halide of titanium tetrahalide is chlorine.

26. The immobilized enzyme system prepared by the method of claim 9.

27. The immobilized enzyme system of claim 26 where the oxide is alumina.

28. The immobilized enzyme system of claim 26 where the diamine is an alkylene diamine whose formula is $H_2N(CH_2)_nNH_2$, where n is an integer from 2 to about 10.

29. The immobilized enzyme system of claim 28 where the diamine is selected from the group consisting of 1,4-diaminobutane, 1,5-diaminopentane, and 1,6-diaminohexane.

30. The immobilized enzyme system of claim 26 where the diamine is a phenylenediamine.

31. The immobilized enzyme system of claim 26 where the bifunctional reagent is selected from the group consisting of succindialdehyde, glutaraldehyde, adipaldehyde, phthalaldehyde, and phenylisocyanate.

32. The immobilized enzyme system of claim 26 where the halide of titanium tetrahalide is selected from the group consisting of fluorine, chlorine, and bromine.

33. The immobilized enzyme system of claim 32 where the halide of titanium tetrahalide is chlorine.

34. The immobilized enzyme system of claim 26 where the enzyme is selected from the group consisting of glucose isomerase, glucoamylase, cholesteroloxidase, alcohol dehydrogenase, amino acid oxidase, arginase, asparaginase, catalase, chymotrypsin, cellulase, collagenase, deoxyribonuclease, ficin, histidase, glucose oxidase, lactase, peroxidase, lysozyme, amylase, papain, rennin, ribonuclease, and urease.

* * * * *